United States Patent
Chou et al.

(10) Patent No.: US 11,484,340 B2
(45) Date of Patent: Nov. 1, 2022

(54) ARTHROSCOPIC CANNULA

(71) Applicant: Kaohsiung Medical University, Kaohsiung (TW)

(72) Inventors: Pei-hsi Chou, Kaohsiung (TW); Cheng-chang Lu, Kaohsiung (TW); Yu-chuan Lin, Kaohsiung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 624 days.

(21) Appl. No.: 16/471,182

(22) PCT Filed: Dec. 19, 2016

(86) PCT No.: PCT/CN2016/110708
§ 371 (c)(1),
(2) Date: Jun. 19, 2019

(87) PCT Pub. No.: WO2018/112690
PCT Pub. Date: Jun. 28, 2018

(65) Prior Publication Data
US 2019/0388119 A1 Dec. 26, 2019

(51) Int. Cl.
*A61B 17/34* (2006.01)
*A61B 17/04* (2006.01)
*A61B 17/00* (2006.01)

(52) U.S. Cl.
CPC ...... *A61B 17/3472* (2013.01); *A61B 17/0401* (2013.01); *A61B 17/3423* (2013.01); *A61B 2017/00862* (2013.01); *A61B 2017/0409* (2013.01); *A61B 2217/005* (2013.01)

(58) Field of Classification Search
CPC ......... A61B 17/04; A61B 17/34; A61B 17/94; A61B 17/3472; A61B 17/0401; A61B 17/3423; A61B 2017/00862; A61B 2017/0409; A61B 2017/0414
See application file for complete search history.

(56) References Cited

U.S. PATENT DOCUMENTS

| | | | |
|---|---|---|---|
| 2005/0216028 A1* | 9/2005 | Hart | A61B 17/3462 606/108 |
| 2007/0282266 A1* | 12/2007 | Davidson | A61B 17/3421 604/164.01 |
| 2010/0249930 A1 | 9/2010 | Myers | |

* cited by examiner

*Primary Examiner* — Vi X Nguyen
(74) *Attorney, Agent, or Firm* — WPAT, PC

(57) ABSTRACT

Disclosed is an arthroscopic cannula to solve the problem of more wounds being created due to the use of a plurality of cannulas in a conventional arthroscopic surgery. The arthroscopic cannula includes a cannula body, a spacer provided inside the cannula body and extending axially along the cannula body to divide an internal space of the cannula body into a first chamber and a second chamber, and a joint connected to one end of the cannula body. The interior of the joint intercommunicates with the first chamber and the second chamber.

6 Claims, 18 Drawing Sheets

ARTHROSCOPIC CANNULA

TECHNICAL FIELD

The present invention relates to a surgical device and, more particularly, to an arthroscopic cannula for being threaded through by instruments or threads during arthroscopic surgery.

BACKGROUND TECHNIQUE

Current techniques for arthroscopic repairing surgery generally use a suture anchor rope tying for the surgery. The suture anchor having a thread penetrates the soft tissues, allowing the soft tissues to be tied and fixed by the thread. Among them, to reduce the amount of the suture anchors used, each suture anchor is generally provided with four threads. Therefore, special attention must be paid in regard to the entangling of the threads to avoid surgical failure.

As shown in FIG. 1, it is a conventional arthroscopic cannula 9, which includes a hollow tube 91 and a plug cap 92 connected to one end of the hollow tube 91. One embodiment similar to the conventional arthroscopic cannula 9 is disclosed in U.S. Pat. No. 8,377,089.

To avoid the entangling of the threads mentioned above which takes place during the surgery, at least two conventional arthroscopic cannulas 9 (which are described as "first cannula 9a" and "second cannula 9b" hereinafter) should be used in the current arthroscopic surgery. That is, after the suture anchor N is inserted into the soft tissue B of the patient, the body of the patient has four threads R1, R2, R3 and R4 connected to the suture anchor N. Among them, the two threads R1 and R2 are two segments of the same thread, and the other two threads R3 and R4 are two segments of the other thread. In the beginning, an instrument is used and inserted through the first cannula 9a into the patient's body to clamp and thread the thread R1 through the soft tissue T. Then, the thread R1 is pulled into the second cannula 9b, allowing a free end of the thread R1 to be pulled out of the patient's body.

As shown in FIG. 2, the instrument is used and inserted through the first cannula 9a and into the patient's body to clamp and thread the thread R3 through the soft tissue T. Then, the thread R3 is pulled back into the first cannula 9a, allowing a free end of the thread R3 to be pulled out of the patient's body.

As shown in FIG. 3, an instrument is used and inserted through the first cannula 9a and into the patient's body to clamp and thread the thread R4. Then, the thread R4 is pulled into the first cannula 9a, allowing a free end of the thread R4 to be pulled out of the patient's body for tying the thread R3 and the thread R4 into a knot. Then, the knot is pushed back into the patient's body through the first cannula 9a. As shown in FIG. 4, the soft tissue T is pulled towards the suture anchor N by the thread R3 and the thread R4 and is fixed in place.

As shown in FIG. 5, an instrument is used again and inserted through the first cannula 9a into the patient's body to thread the thread R1 and the thread R2 at the same time, and the thread R1 and the thread R2 are pulled into the first cannula 9a, allowing the thread R1 and the thread R2 to be tied into a knot outside the patient's body. Then, the knot is pushed back into the patient's body through the first cannula 9a. As shown in FIG. 6, the thread R1, the thread R2 and the soft tissue T are pulled towards the suture anchor N and are fixed in place.

Accordingly, the entangling of the threads may be effectively avoided. However, since this requires at least two current arthroscopic cannulas, an incision should be created on the patient's body for each arthroscopic cannula. This leads to long surgery time and damage to the joint tissue and increases the hurt area. Therefore, it is necessary to improve the arthroscopic cannula.

SOLUTION TO PROBLEMS

Technical Solution

To overcome the above-mentioned problems, the present invention provides an arthroscopic cannula having dual chambers that separate different threads, thereby reducing the quantity of the cannulas required during the surgery in half.

An arthroscopic cannula of the present invention includes a cannula body, a spacer mounted in the cannula body and extending in an axial direction of the cannula body to divide an internal space of the cannula body into a first chamber and a second chamber, and a joint connecting with one end of the cannula body. The spacer is configured to move perpendicularly to an axial direction of the cannula body to change cross-sectional areas of the first chamber and the second chamber. The interior of the joint intercommunicates with the first chamber and the second chamber.

Accordingly, the interior of the arthroscopic cannula of the present invention has dual chambers that separate different threads. Thus, it may not only avoid the entangling of different threads, but also reduce the quantity of the cannulas required during the surgery in half to reduce the number of the incision created on the patient's body. This may reduce the quantity of the cannulas required during the surgery in half, thereby reducing the surgery time and the hurt area and lowering the probabilities of surgical complications and wound infection.

Alternatively, the spacer may be a thin film. Two lateral faces of the spacer respectively extend in an axial direction of the cannula body and connect to an inner surface of the cannula body. The spacer has an end edge extending from one of the lateral edges to the other of the lateral edges. The length of the end edge is larger than an inner diameter of the cannula body. This structure makes the spacer positioned in the cannula body in a curly manner such that the spacer can be pushed to move perpendicularly to the axial direction of the cannula body to change the cross-sectional areas of the first and second chambers, attaining the advantages including improved convenience in operation.

Alternatively, the spacer may be an elastic film. The two lateral faces of the spacer respectively extends in an axial direction of cannula body and connects to an inner surface of the cannula body. Accordingly, the spacer may deform elastically to change the cross-sectional areas of the first and second chambers when pushed by the instrument, attaining the advantages including improved convenience in operation.

Alternatively, the two lateral edges of the spacer are positioned diametrically oppositely to each other in radial directions of the cannula body to allow for equal change in cross-sectional areas of the first and second chambers, improving convenience in operation.

Alternatively, the spacer may be a flexible tube having an outer circumferential length smaller than an inner circumferential length of the cannula body. An outer circumferential face of the spacer is partially connected to an inner surface of the cannula body. Accordingly, the portion of the outer circumferential face of the spacer which is not connected to the cannula body may be pushed to move perpendicularly to the axial direction of the cannula body, changing the cross-sectional areas of the first and second chambers. Thus, the advantages including improved convenience in operation are attained.

ADVANTAGEOUS EFFECT OF THE INVENTION

Advantageous Effect

The present invention may not only efficiently avoid the entangling among different threads, but also reduces the quantity of the cannula required during the surgery in half to reduce the number of the incision created on the patient's body, thereby reducing the surgery time, the hurt area and the damage to the joint tissue. This can lower the probabilities of surgical complications and wound infections.

BRIEF DESCRIPTION OF THE ACCOMPANYING DRAWINGS

Description of the Accompanying Drawings

BEST EMBODIMENT FOR CARRYING OUT THE INVENTION

Best Implementation of the Invention

To make the aforementioned and other objectives, characteristics and advantages of the invention obvious and to facilitate the understanding of said objectives, characteristics and advantages, the preferred embodiments of the invention are elaborated below with the accompanying drawing.

Figure 1:
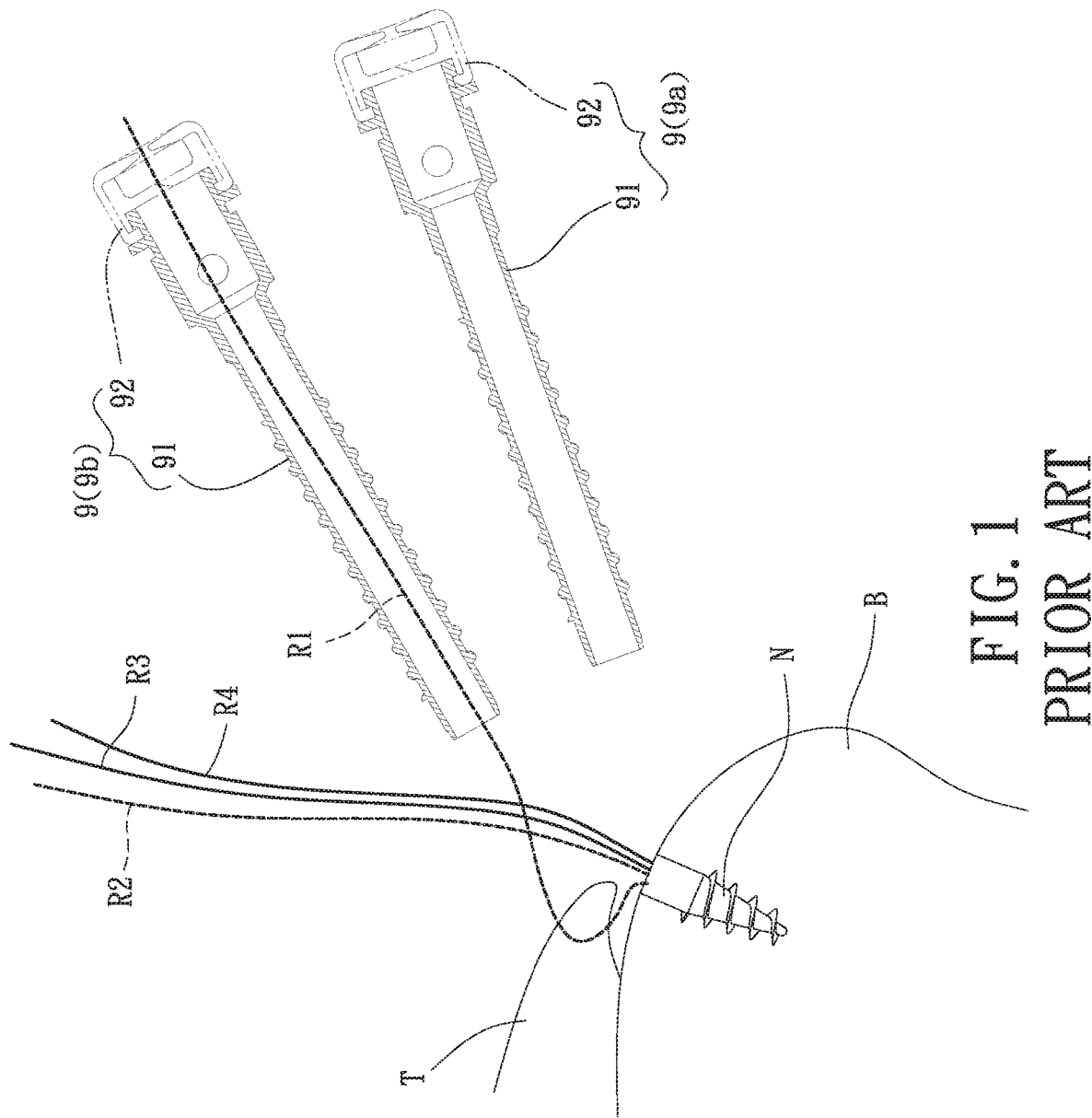
FIG. 1 is a first diagrammatic view of an implementation of a conventional arthroscopic cannula.
Figure 2:
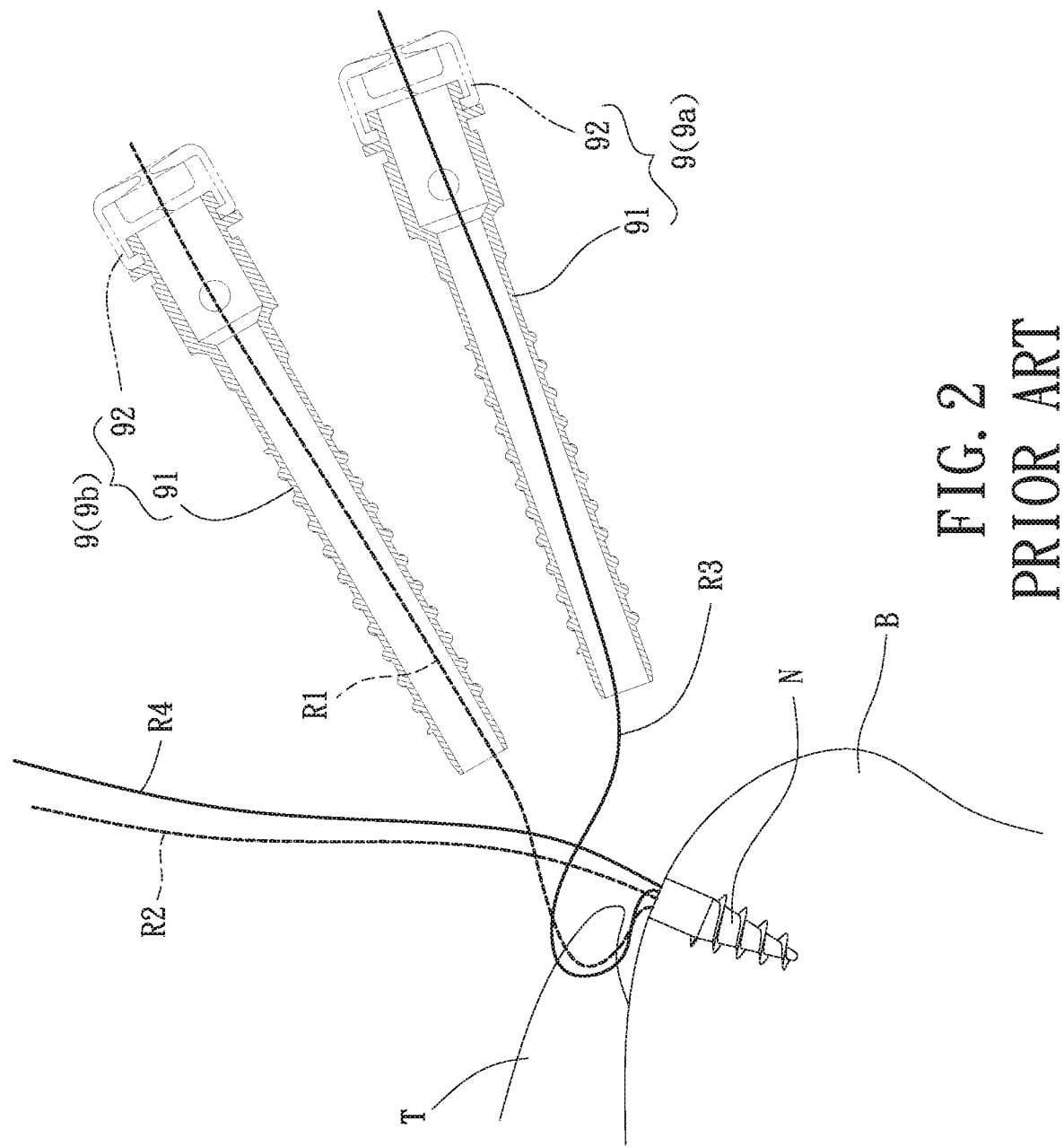
FIG. 2 is a second diagrammatic view of an implementation of a conventional arthroscopic cannula.
Figure 3:
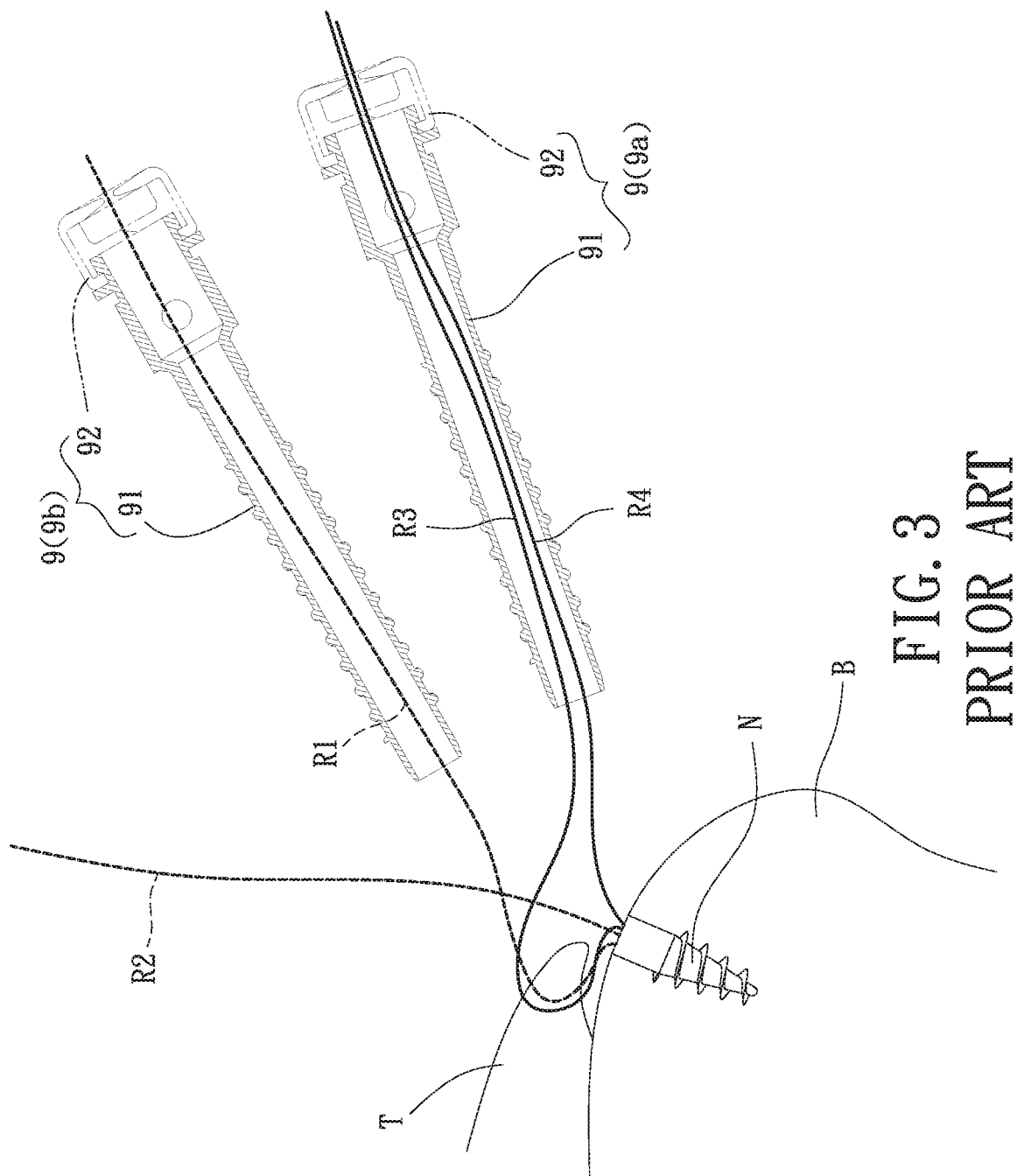
FIG. 3 is a third diagrammatic view of an implementation of a conventional arthroscopic cannula.
Figure 4:
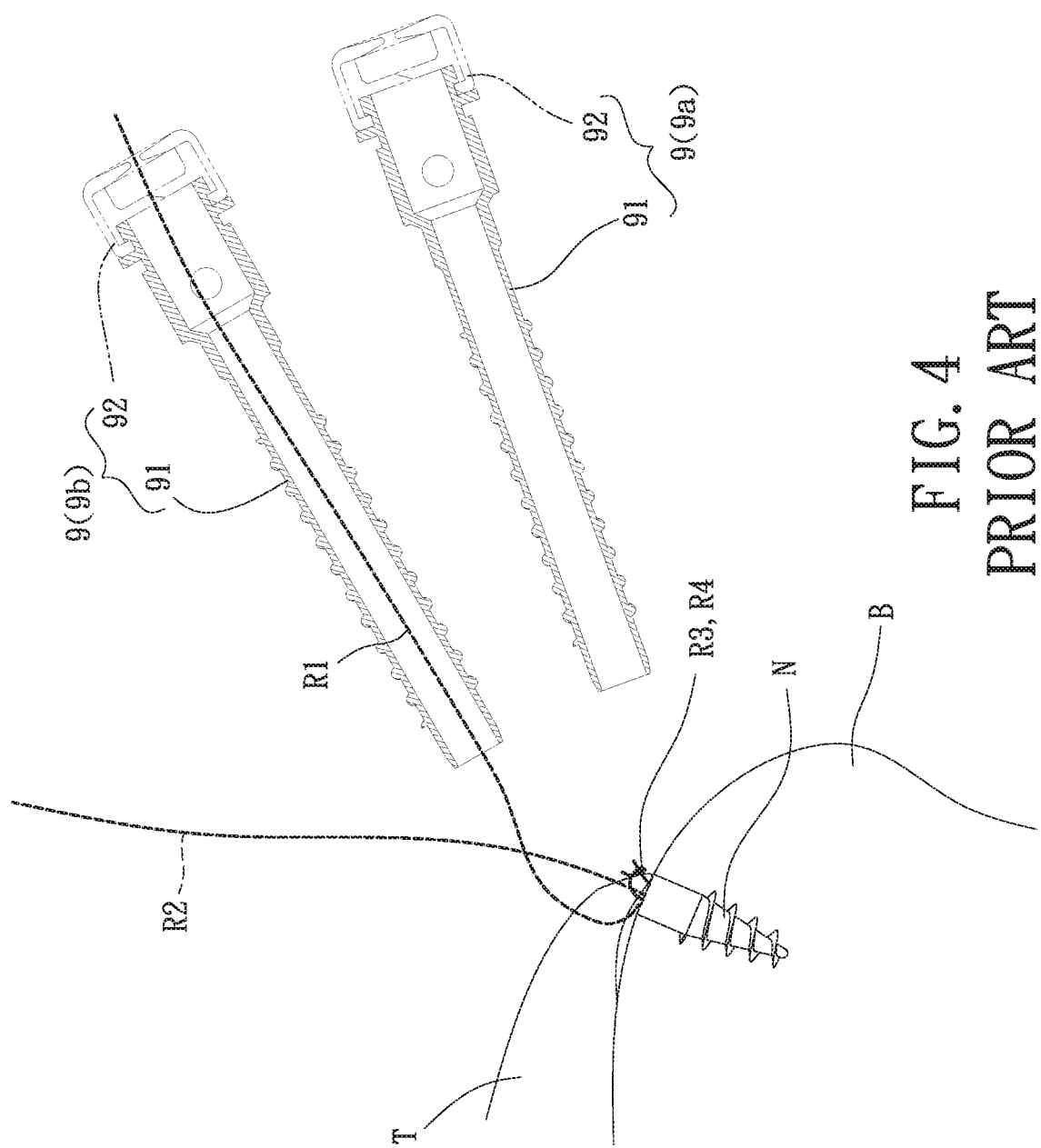
FIG. 4 is a fourth diagrammatic view an implementation of arthroscopic cannula.
Figure 5:
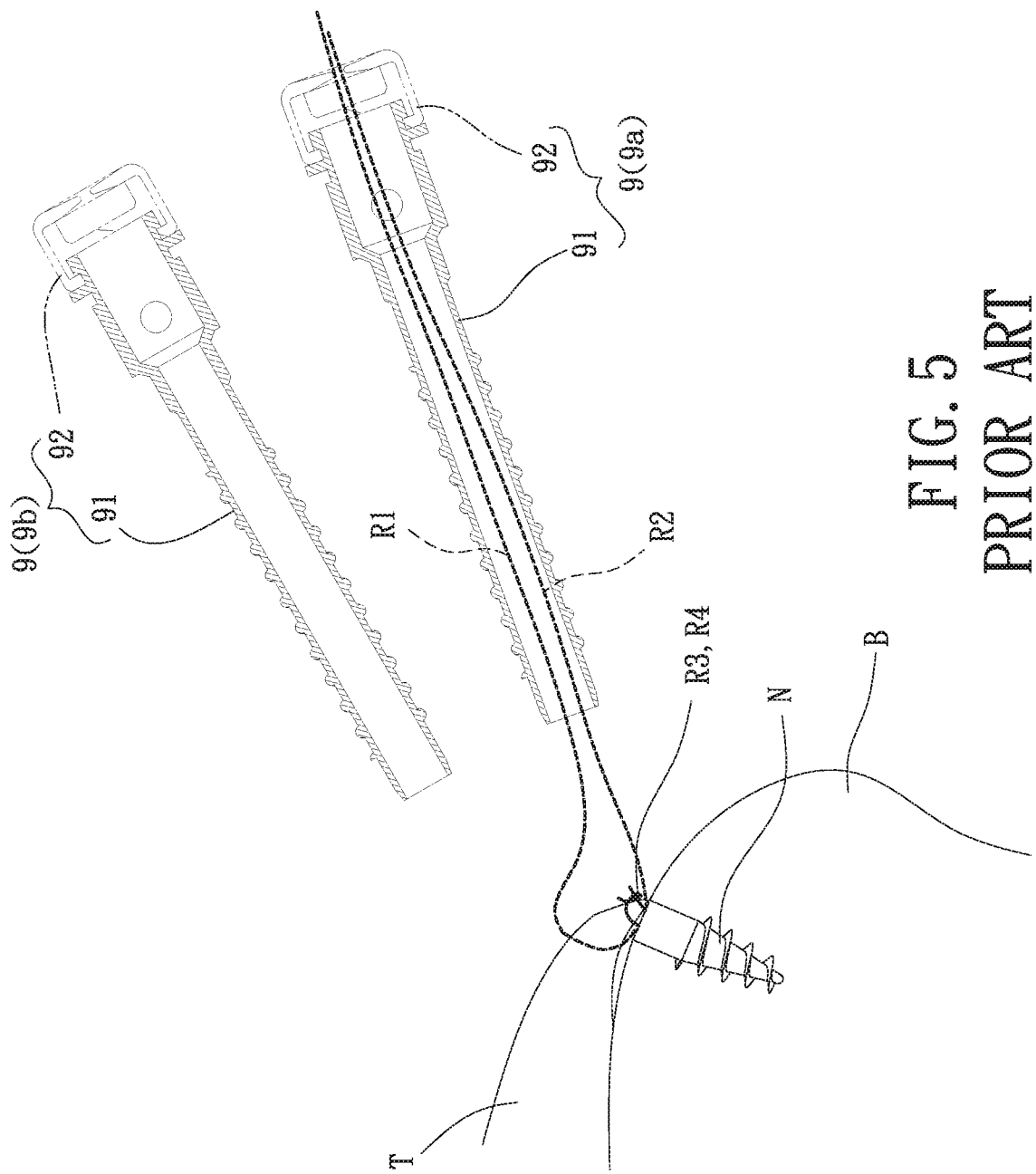
FIG. 5 is a fifth diagrammatic view of an implementation of a conventional arthroscopic cannula.
Figure 6:
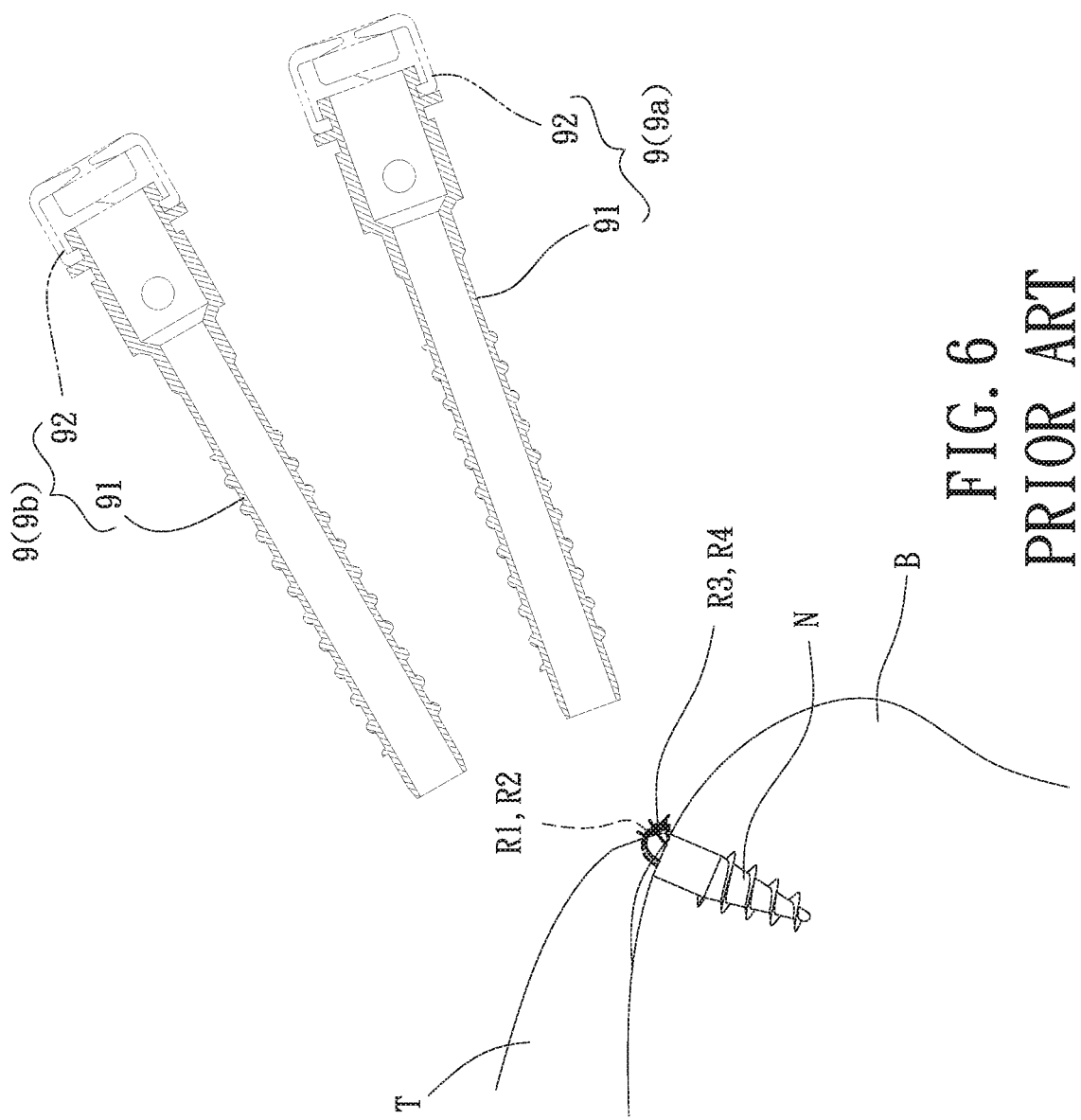
FIG. 6 is a sixth diagrammatic view of an implementation of a conventional arthroscopic cannula.
Figure 7:
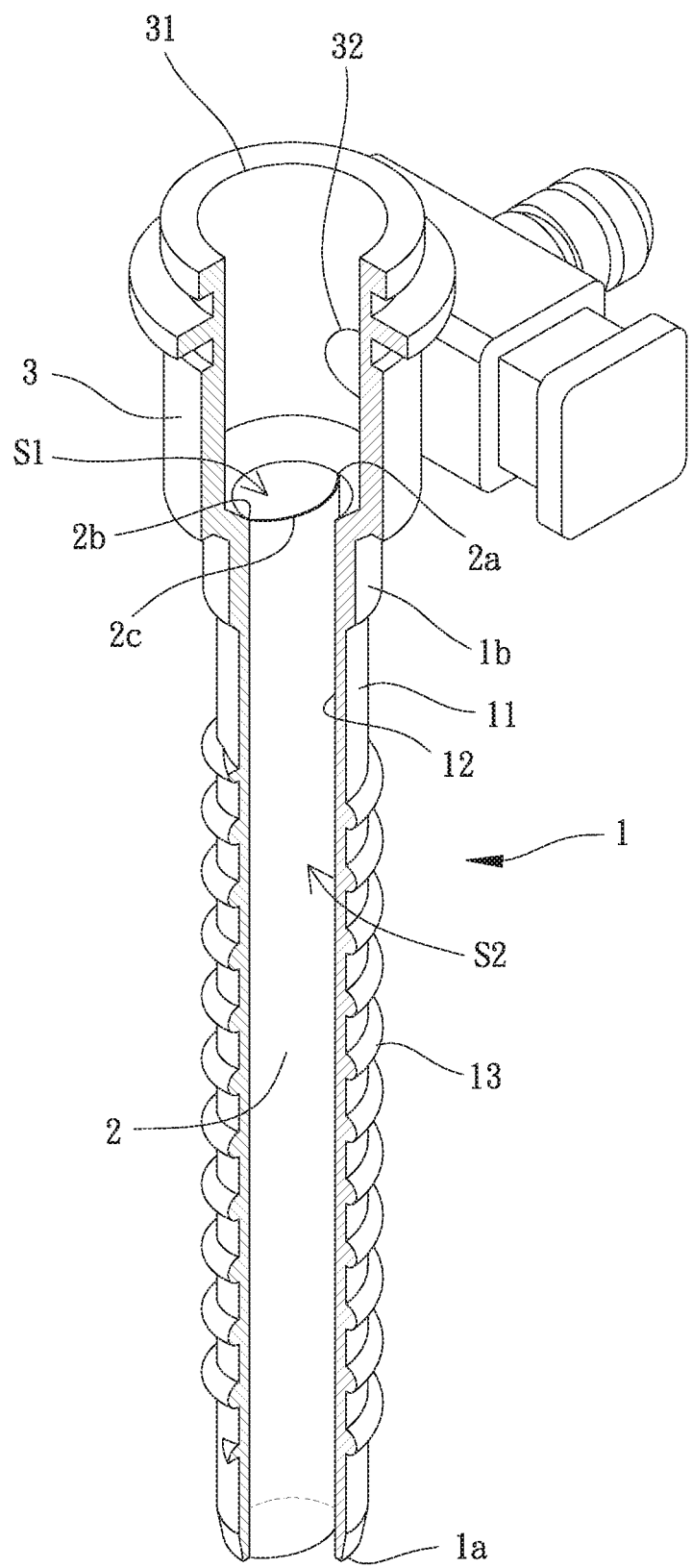
FIG. 7 is a partially cut-off, perspective structural view of a first embodiment according to the present invention.

Please refer to FIG. 7 which shows a first embodiment of the arthroscopic cannula of the present invention. The arthroscopic cannula generally includes a cannula body 1, a spacer 2 and a joint 3. The spacer 2 is disposed in the cannula body 1. The joint 3 connects with one end of the cannula body 1.

Specifically, the cannula body 1 is in the form of a hollow tube having two ends respectively being an insertion end 1a and an exposed end 1b. In the use of the arthroscopic cannula of the present invention during the arthroscopic surgery, the insertion end 1a of the cannula body 1 is inserted into the patient's body while the exposed end 1b of the cannula body 1 remains outside of the patient's body. The cannula body 1 has an outer surface 11 and an inner surface 12 opposite to the outer surface 11. A threaded portion 13 is provided on the outer surface 11 of the cannula body 1 between the insertion end 1a and the exposed end 1b.

Figure 8:
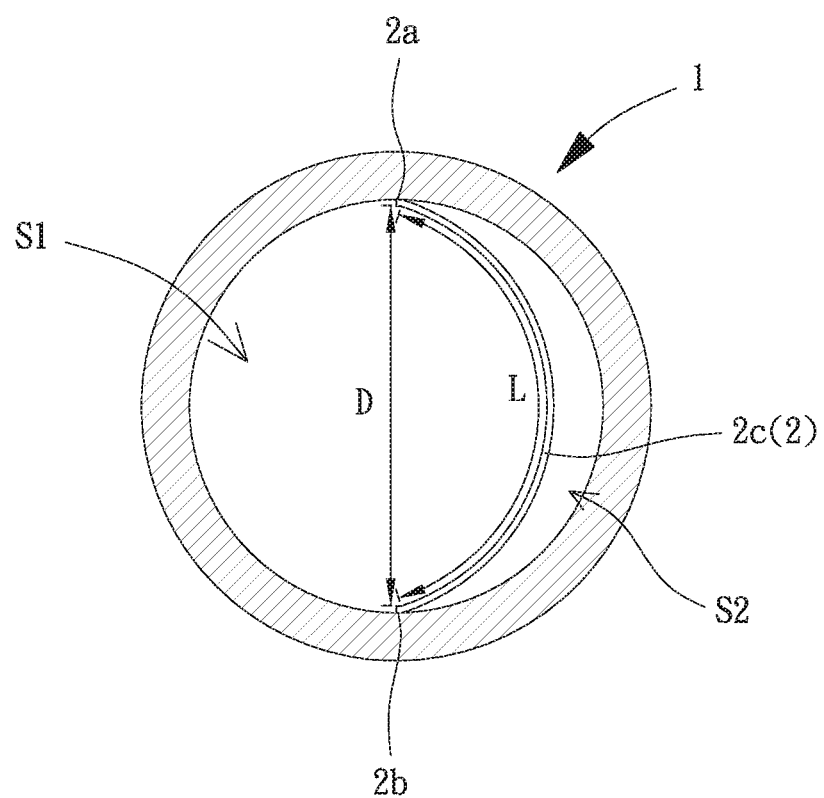
FIG. 8 is a longitudinal cross sectional view of the first embodiment according to the present invention.

Please referring to FIGS. 7 and 8, the spacer 2 is disposed in the cannula body 1 and extends axially along the cannula body 1 to divide an internal space of the cannula body 1 into a first chamber S1 and a second chamber S2. The first chamber S1 and the second chamber S2 respectively extend axially along the cannula body 1 to intercommunicate with the interior and exterior spaces of the cannula body 1. As such, different threads may be disposed in different spaces during the arthroscopic surgery to avoid entangling among different threads.

In the present embodiment, the spacer 2 may be a thin film. Two lateral edges 2a and 2b of the spacer 2 respectively extend axially along the cannula body 1 and connect to the inner surface 12 of the cannula body 1. The spacer 2 has an end edge 2c extending from one of the lateral edges 2a to the other lateral edge 2b. The length L of the end edge 2c is larger than the inner diameter D of the cannula body 1, allowing the spacer 2 to be disposed in the cannula body 1 in an arc shape and to be moved axially along the cannula body 1 by slightly moving the spacer 2. The spacer 2 may be a thin film which is inflexible and may maintain a designed size. Alternatively, the spacer 2 may be an elastic film which is flexible, as long as the spacer 2 can be pushed to move axially along the cannula body 1. This is not used to limit the present invention.

Accordingly, the spacer 2 may be pushed to move perpendicularly to the axial direction of the cannula body 1 to change the cross-sectional areas of the first chamber S1 and the second chamber S2. In other words, when the spacer 2 is moved towards the second chamber S2, the cross sectional area of the first chamber S1 becomes larger. Oppositely, the cross sectional area of the second chamber S2 becomes smaller. When the spacer 2 is pushed towards the first chamber S1, the cross-sectional area of the second chamber S2 becomes larger. Oppositely, the cross-sectional area of the first chamber S1 becomes smaller. Two lateral edges 2a and 2b of the spacer 2 are disposed oppositely in the cannula body 1 to allow for equal change in cross-sectional areas of the first chamber S1 and the second chamber S2, enhancing convenience in operation.

Referring to FIG. 7 again, the joint 3 connects to one end of the cannula body 1. The interior of the joint 3 intercommunicates with the first chamber S1 and the second chamber S2. The joint 3 has an insertion opening 31 opposite to the first chamber S1 and the second chamber S2, allowing for insertion of the instrument into the interior of the joint 3 as well as further insertion towards the first chamber S1 or the second chamber S2 of the cannula body 1, so as to extend out of the insertion end 1a of the cannula body 1. The joint 3 further includes an infusion opening 32 intercommunicating with the interior of the joint 3 and located between the insertion port 31 and the cannula body 1. The infusion opening 32 may be provided to connect to a liquid suction device (not shown in FIG. 7), which permits the liquid to be injected into the interior of the joint 3 and to flow to the first chamber S1 and the second chamber S2, or permits the liquid to be drawn into the interior of the joint 3 from the first chamber S1 and the second chamber S2 and then to be output through the infusion opening 32.

Figure 9:
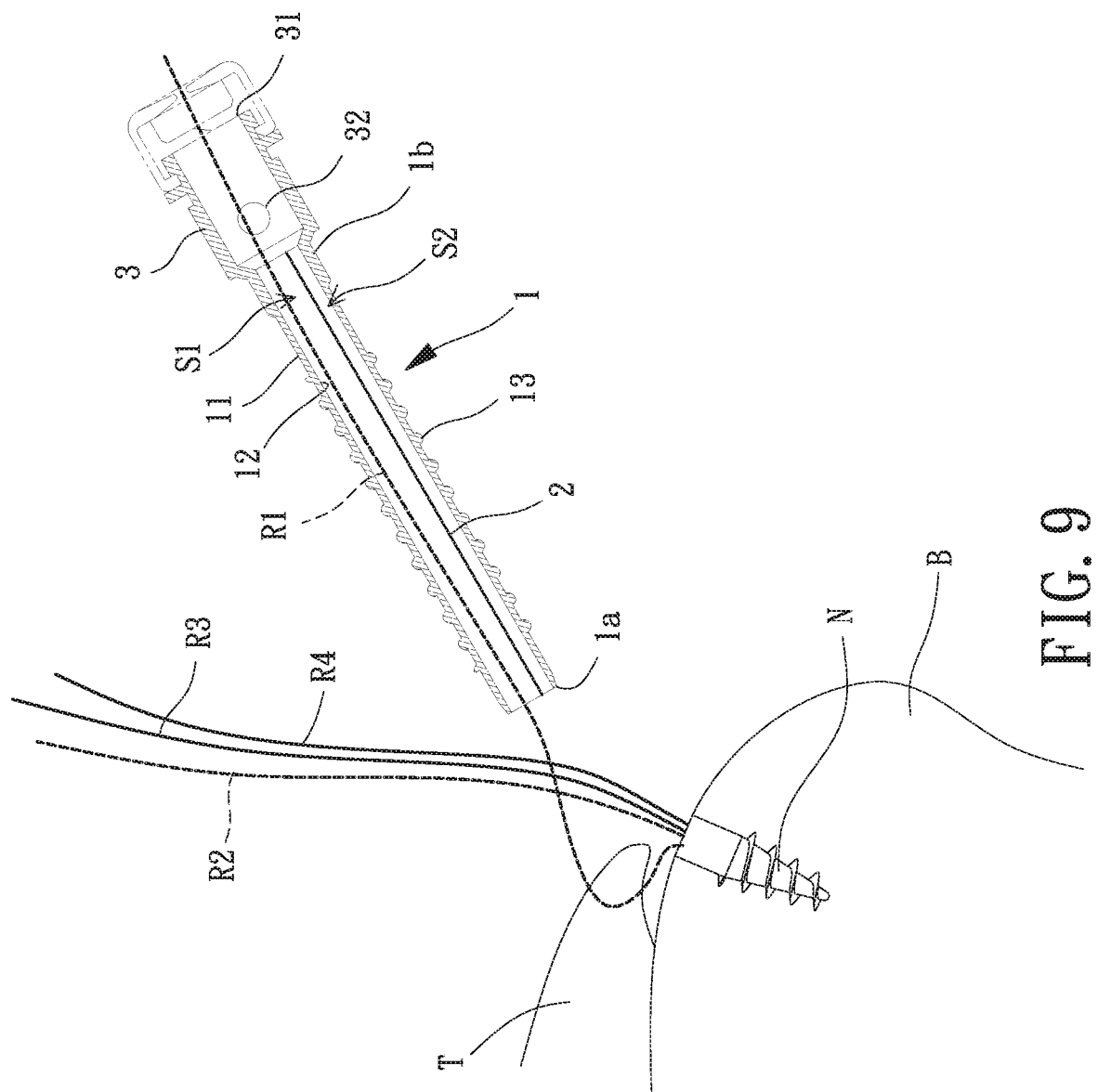
FIG. 9 is a diagrammatic view of an implementation of the first embodiment according to the present invention.

Referring to FIG. 9, according to the structure mentioned above, during the arthroscopic surgery, an operation wound may be created on the patient's body in which the arthroscopic cannula of the present invention is positioned on the operation wound, allowing the insertion end 1a of the cannula body 1 to be inserted into the patient's body while remaining the exposed end 1b of the cannula body 1 and the joint 3 outside of the patient's body. The cannula body 1 has an outer surface 11 and an opposite inner surface 12. A threaded portion 13 is positioned between the insertion end 1a and the exposed end 1b of the outer surface 11 of the cannula body 1.

Figure 10:
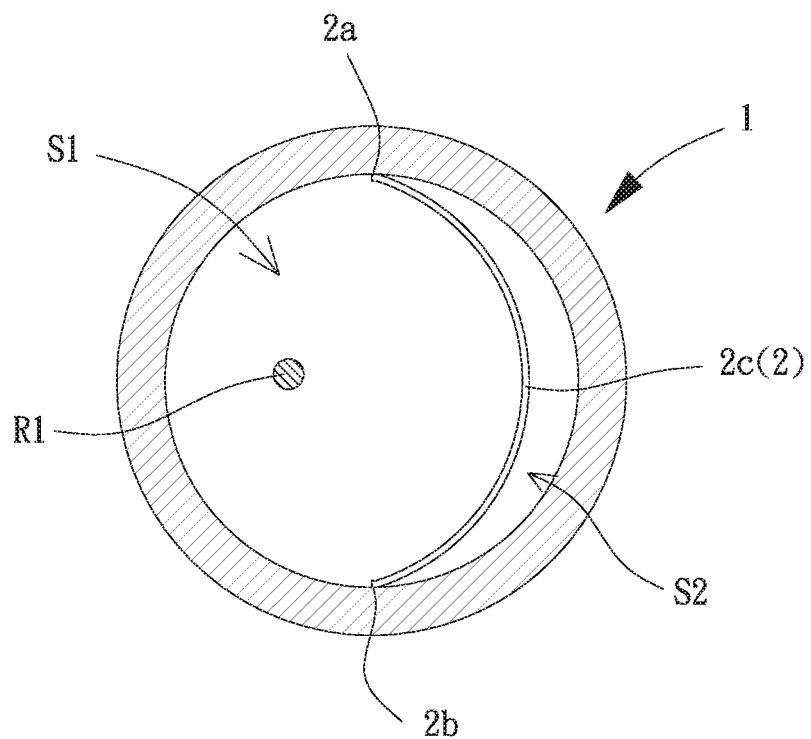
FIG. 10 is a longitudinal cross sectional view in the state of FIG. 9.

Referring to FIGS. 9 and 10, in the binging, a suture anchor N is implanted into the bone tissue B, allowing the four threads R1, R2, R3 and R4, that are connected to the suture anchor N, to remain in the patient's body. Among them, the two threads R1 and R2 are two segments of the same thread, and the other two threads R3 and R4 are two segments of the other thread. Furthermore, an instrument (not shown) is inserted through the insertion port 31 of the joint 3 and the spacer 2 is moved towards the chamber S2 to increase the cross-sectional area of the first chamber S1, permitting the instrument to be inserted through the first chamber S1 into the patient's body to clamp and thread the thread R1 through the soft tissue T. Then, the thread R1 is clamped into the first chamber S1 by the instrument, allowing a free end of the thread R1 to be threaded out of the patient's body through the first chamber S1 and the insertion port 31 of the joint 3.

Figure 11:
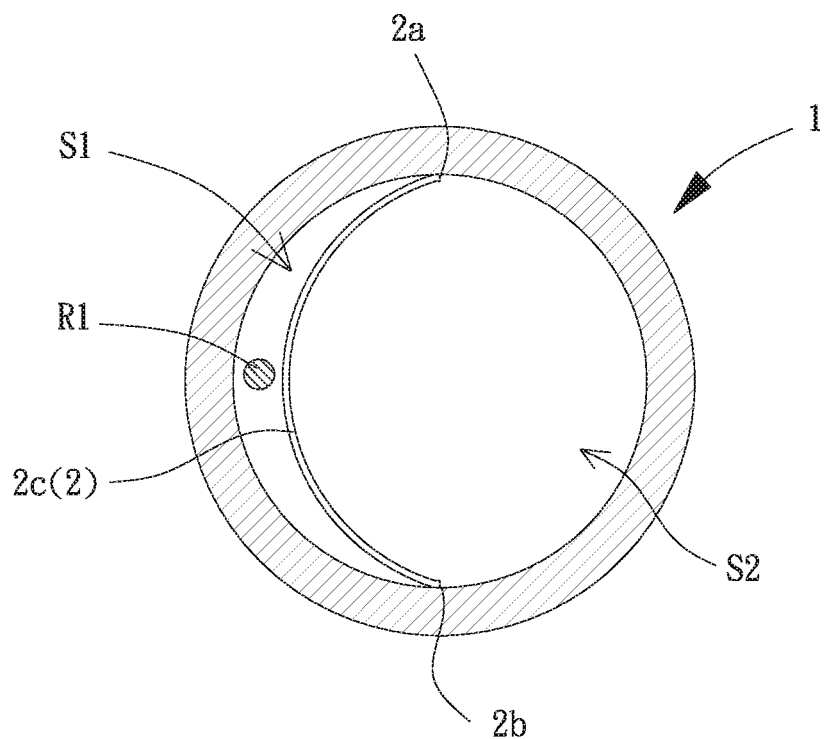
FIG. 11 is a diagrammatic view of an implementation where the spacer of FIG. 10 is pushed towards another side.
Figure 12:
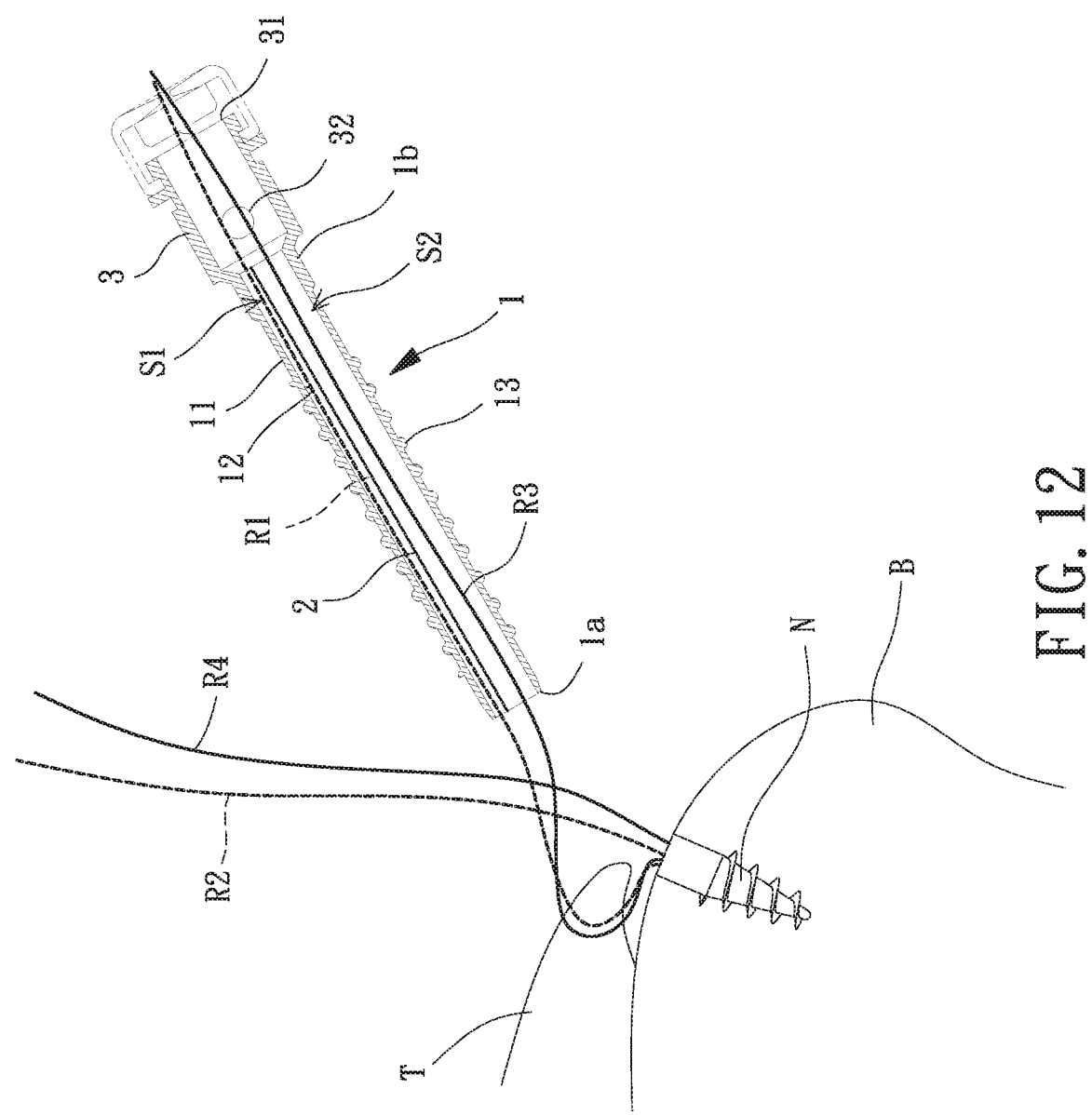
FIG. 12 is a diagrammatic view of a second implementation of the first embodiment according to the present invention.

Referring to FIGS. 11 and 12, the instrument is used again to push the spacer 2 towards the first chamber S1 to increase the cross-sectional area of the second chamber S2 while relatively reducing the cross-sectional area of the first chamber S1. As such, the instrument is inserted through the second chamber S2 and into the patient's body to clamp and thread the thread R3 through the soft tissue T. Then, the thread R3 is clamped back into the second chamber S2 by the instrument to thread a free end of the thread R3 out of the patient's body through the second chamber S2 and the insertion port 31 of the joint 3.

Figure 13:
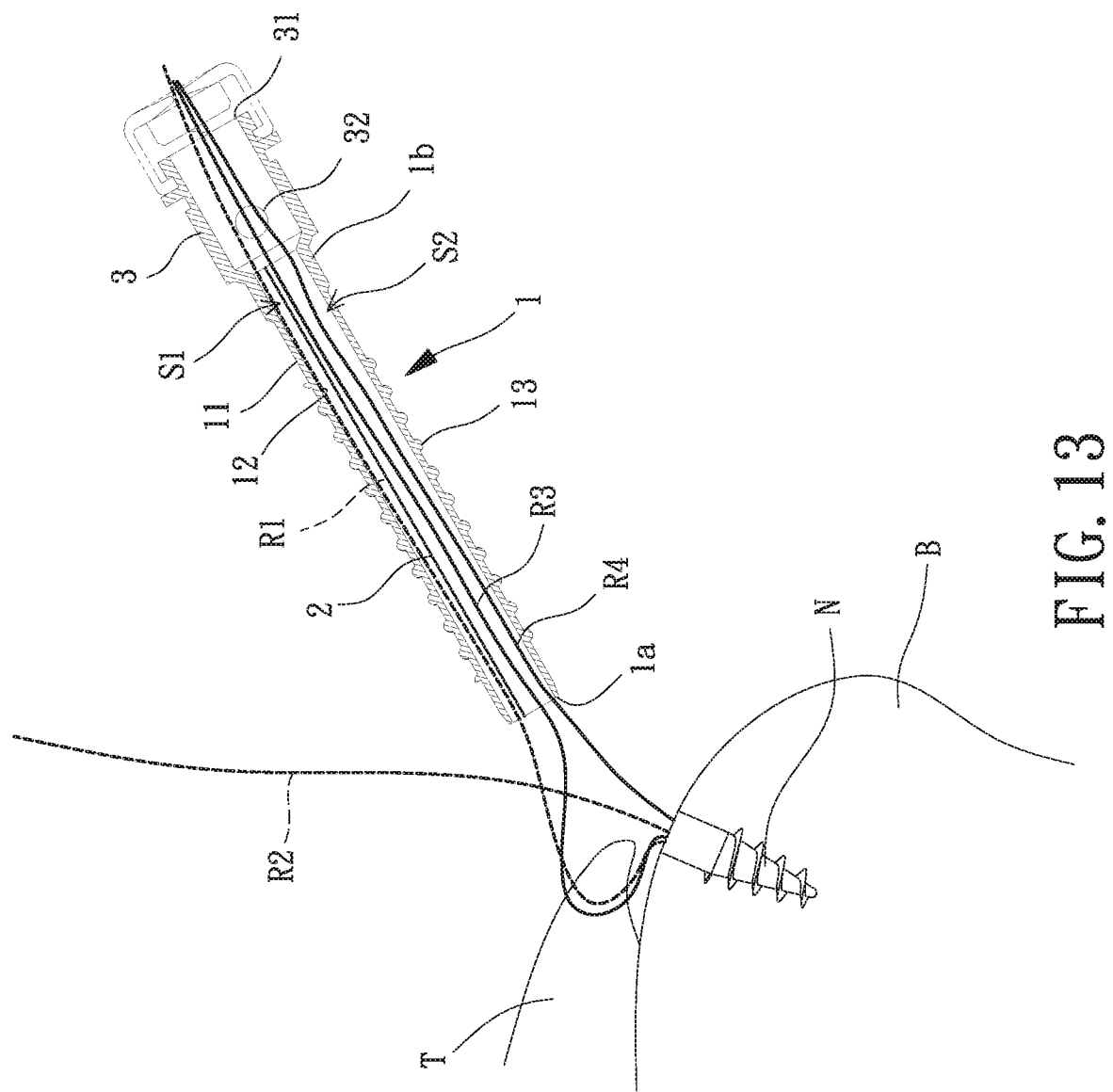
FIG. 13 is a diagrammatic view of a third implementation of the first embodiment according to the present invention.

Referring to FIG. 13, the instrument is used and inserted through the second chamber S2 and into the patient's body to clamp the thread R4 also into the second chamber S2, threading a free end of the thread R4 out of the patient's body through the second chamber S2 and the insertion port 31 of the joint 3.

Figure 14:
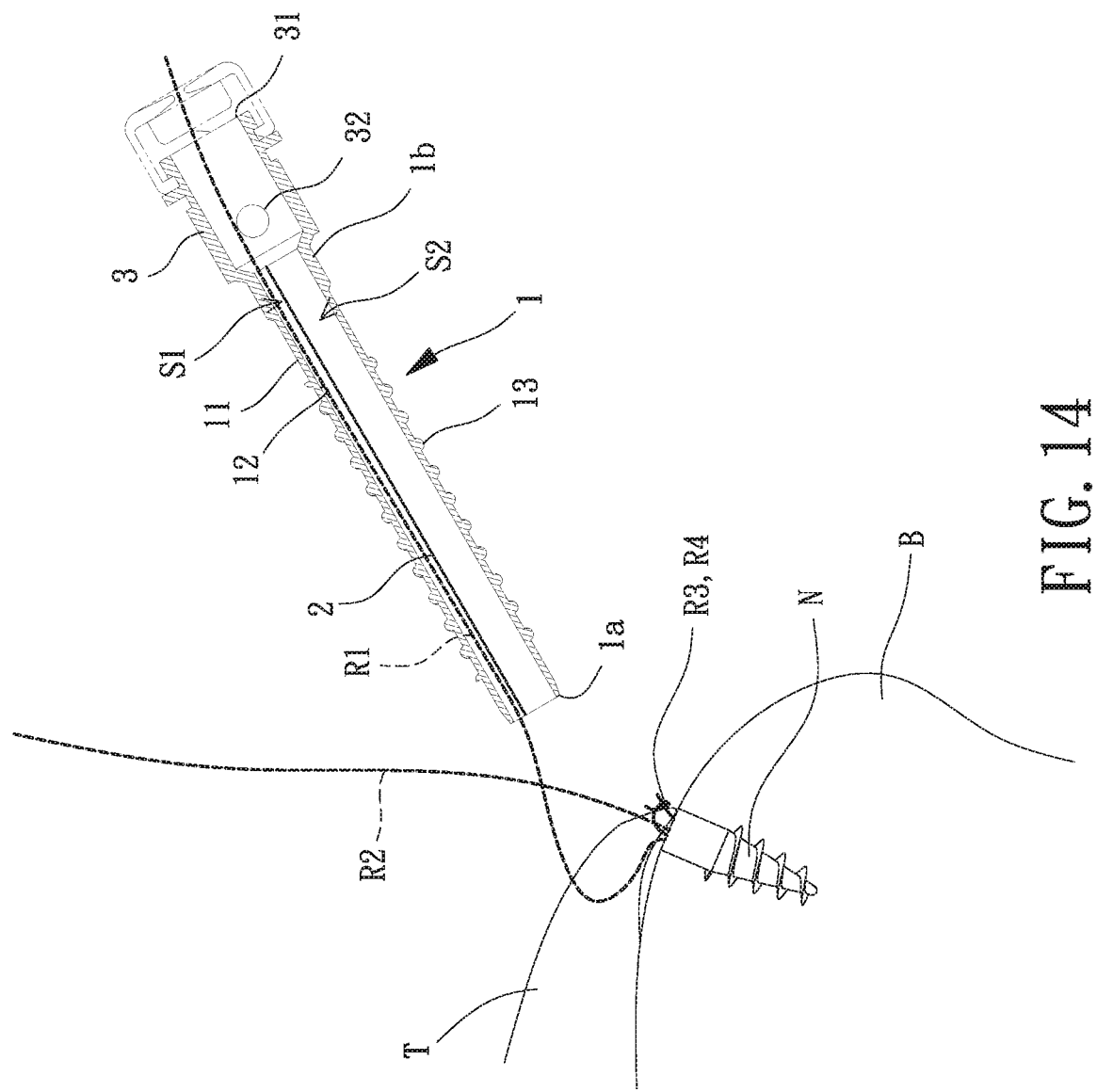
FIG. 14 is a diagrammatic view of a fourth implementation of the first embodiment according to the present invention.

Referring to FIG. 14, the thread R3 and the thread R4 are tied into a knot outside the patient's body. Then, the instrument is used to push the knot back into the patient's body through the second chamber S2, pulling the soft tissue T towards the suture anchor N by the thread R3 and the thread R4 and fixing the soft tissue T in place.

Figure 15:
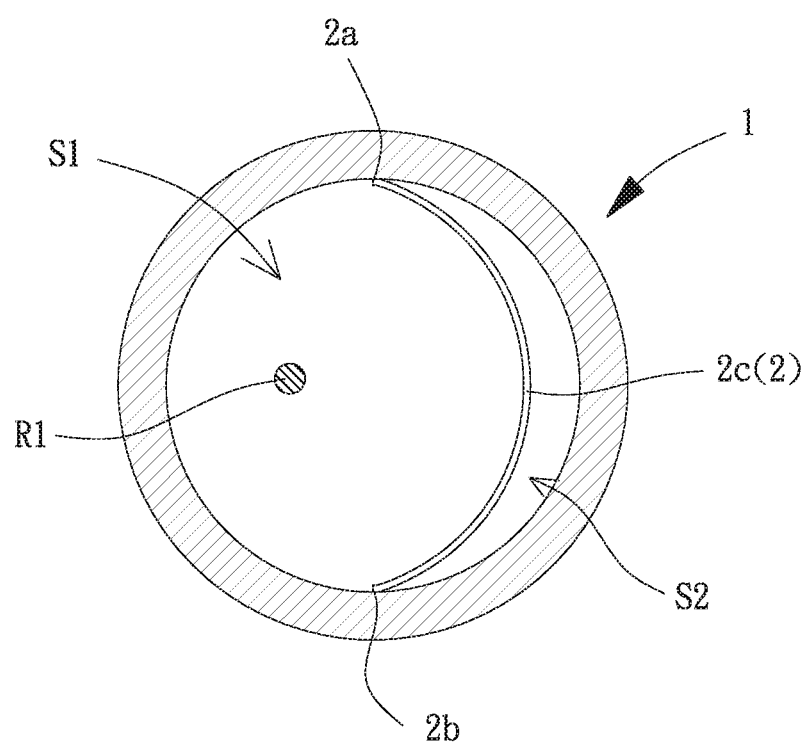
FIG. 15 is a diagrammatic view of an implementation where the spacer of FIG. 14 is pushed towards another side.
Figure 16:
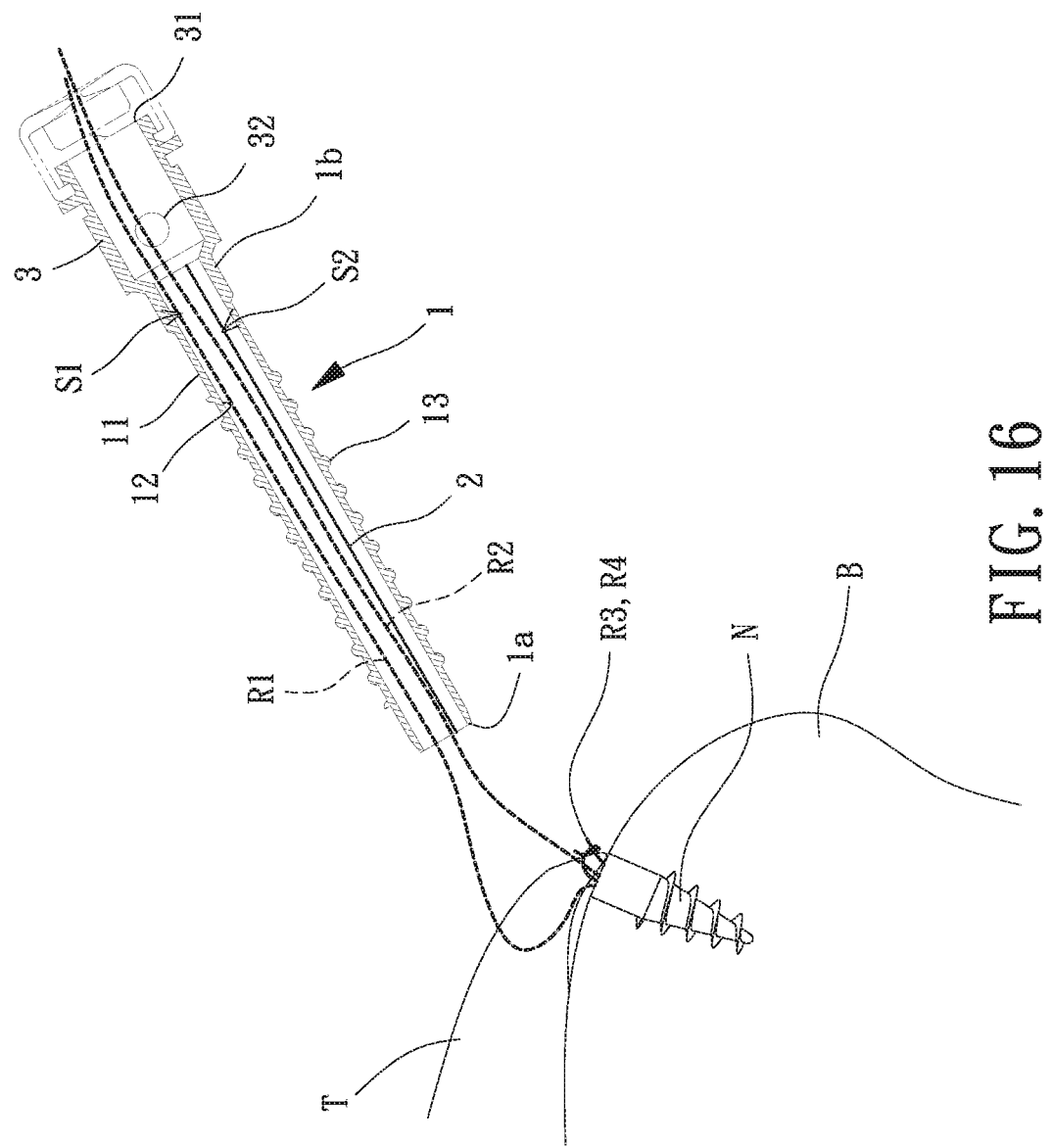
FIG. 16 is a diagrammatic view of a fifth implementation of the first embodiment according to the present invention.
Figure 17:
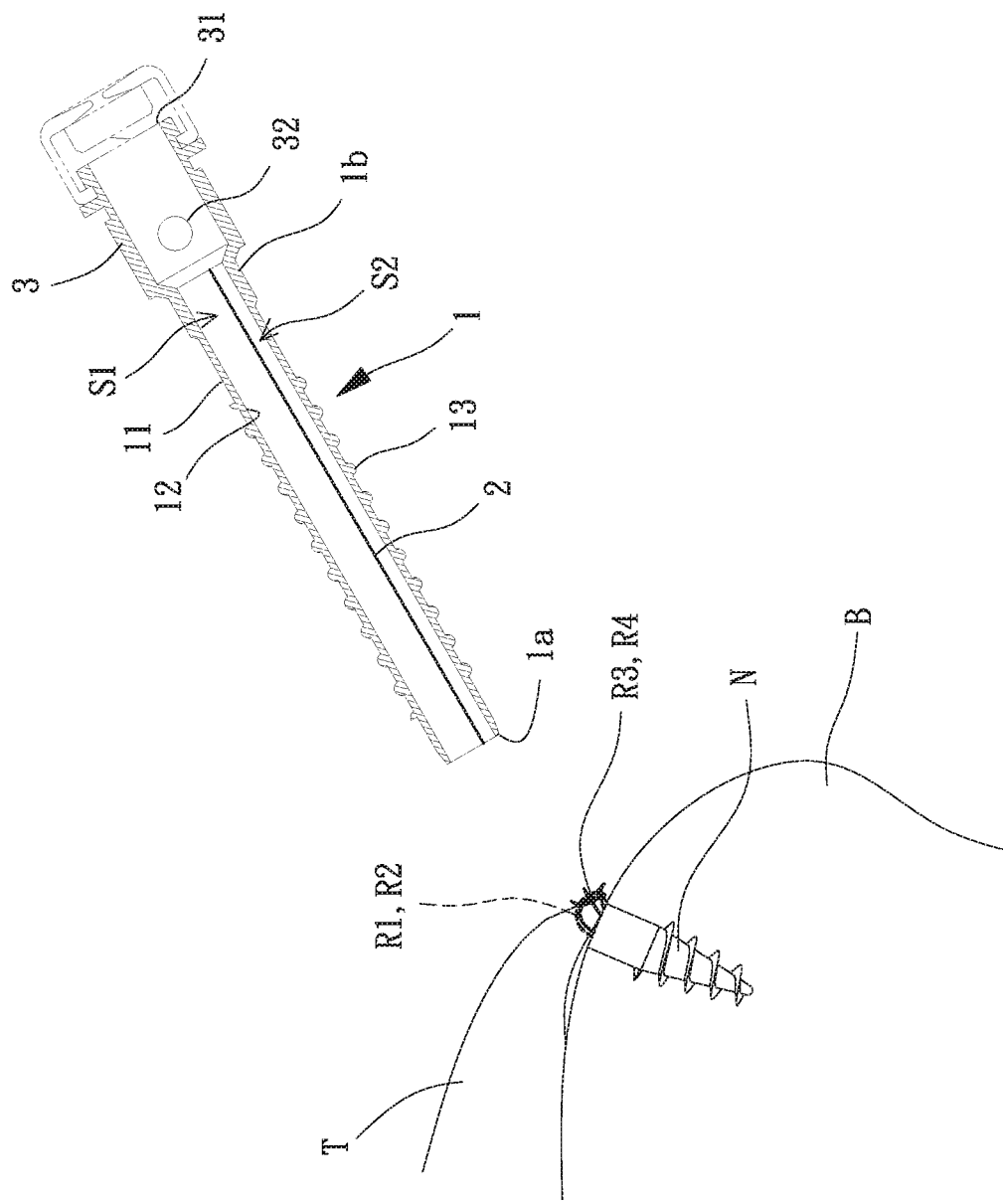
FIG. 17 is a diagrammatic view of a sixth implementation of the first embodiment according to the present invention.

Referring to FIGS. 15 and 16, the instrument is used again to push the spacer 2 towards the second chamber S2 to again increase the cross-sectional area of the first chamber S1 receiving the thread R1 and to relatively reduce the cross-sectional area of the second chamber S2. The instrument is used again and inserted through the patient's body to clamp and thread both the thread R1 and the thread R2 back into the first chamber S1, allowing the thread R1 and the thread R2 to be tied into a knot outside the patient's body. Then, as shown in FIG. 17, the knot is pushed back into the patient's body through the first chamber S1, pulling the soft tissue T towards the suture anchor N and fixing the thread R1 and the thread R2 in place.

Figure 18:
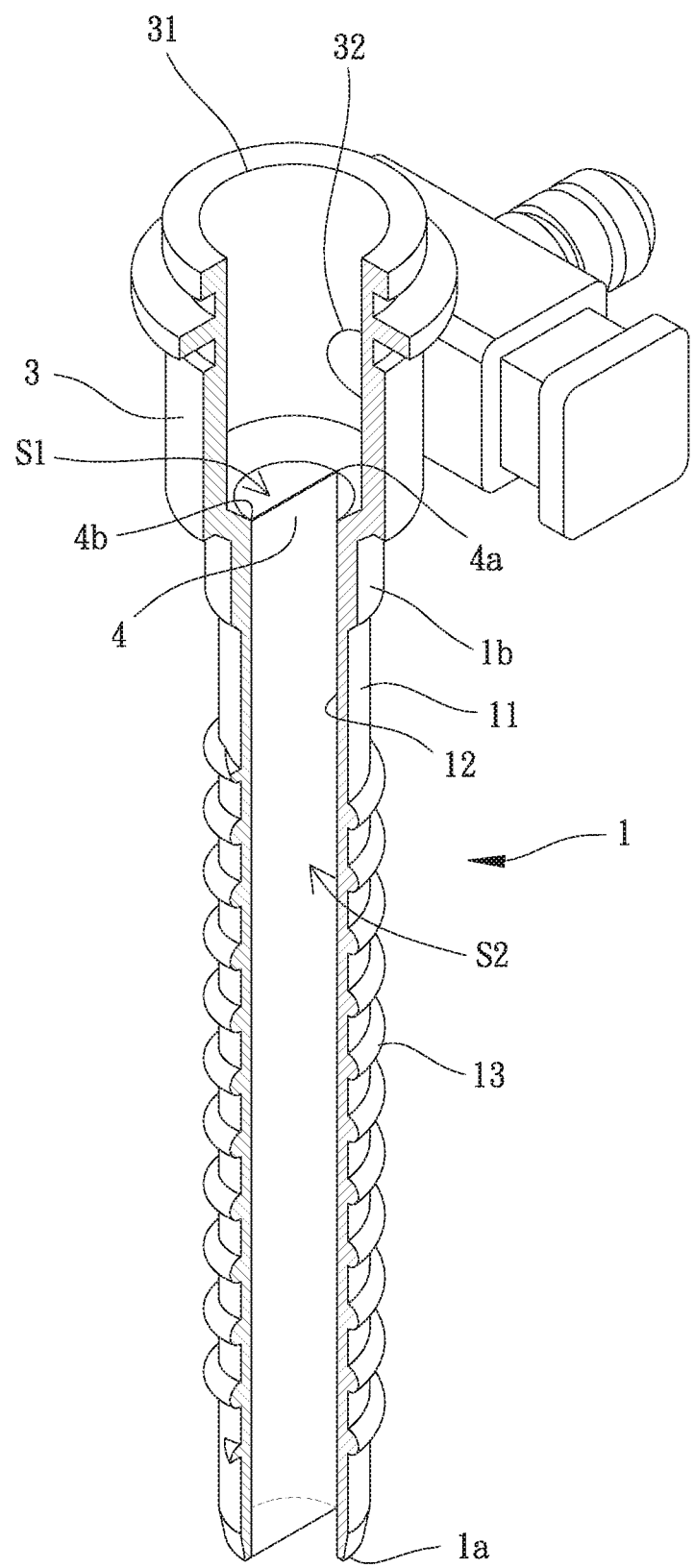
FIG. 18 is a partially cut-off, perspective structural view of the second embodiment according to the present invention.
Figure 19:
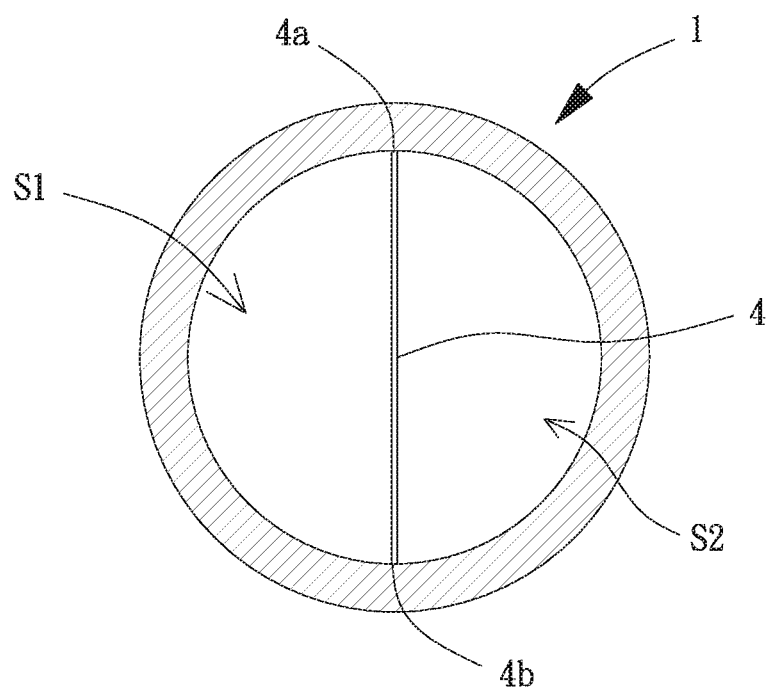
FIG. 19 is a longitudinal cross sectional view of the second embodiment according to the present invention.

Referring to FIGS. 18 and 19 which show a second embodiment of the arthroscopic cannula of the present invention. The second embodiment of the present invention is substantially similar to the first embodiment and mainly differs from the first embodiment in that: an elastic film is used as the spacer 4 in the second embodiment.

Specifically, the spacer 4 itself has great elasticity, and can deform elastically under force to increase the total area. When the force is removed, the spacer 4 can restore its total area where the deformation has not yet taken place. Each of the two lateral edges 4a and 4b of the spacer 4 extends axially along the cannula body 1 and connects to the inner surface 12 of the cannula body 1. Accordingly, the spacer 4 may deform elastically when pushed, thereby changing the cross-sectional area of the first chamber S1 and the second chamber S2. That is, when the instrument is inserted into the first chamber S1, the spacer 4 may deform elastically to increase the cross-sectional area of the first chamber S1 and reduce the cross-sectional area of the second chamber S2. Moreover, when the instrument is pulled, the spacer 4 may automatically restore under elasticity. Therefore, the present embodiment may further eliminate the step of moving the spacer 4 to enhance convenience in operation. Similarly, the two lateral edges 4a and 4b of the spacer 4 are preferably arranged in a diametrically opposite manner to allow for equal change in cross-sectional areas of the first chamber S1 and the second chamber S2, enhancing convenience in operation.

Figure 20:
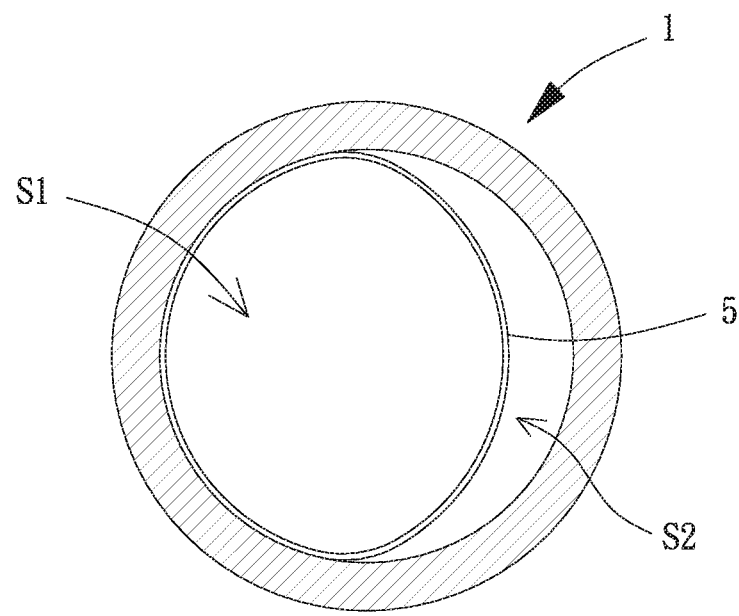
FIG. 20 is a longitudinal cross sectional view of the third embodiment according to the present invention.

Referring to FIG. 20 which shows a third embodiment of the arthroscopic cannula of the present invention. The third embodiment of the present invention is substantially similar to the first embodiment mentioned above and mainly differs from the first embodiment in that: a flexible tube is used as the spacer 5 in the third embodiment.

Specifically, the tube wall of the spacer 5 is thin and soft. The outer circumferential length of the spacer 5 is smaller than the inner circumferential length of the cannula body 1. The outer peripheral face of the spacer 5 is partially connected to the inner surface 12 of the cannula body 1 to form the aforementioned first chamber S1 in the spacer 5 and the aforementioned second chamber S2 between the outer peripheral face of the spacer 5 and the inner surface 12 of the cannula body 1. Accordingly, the portion of the outer circumferential face of the spacer 5 which is not connected to the cannula body 1 may be pushed to move perpendicularly to the axial direction of the cannula body 1, changing the cross-sectional areas of the first chamber S1 and the second chamber S2. Thus, the advantages including improved convenience in operation are attained.

In summary, during the use of the arthroscopic cannula of the present invention, the dual chambers of the single cannula can be used to separate different threads. Therefore, it may not only to avoid the problems of thread entangling, but also to reduce the quantity of the cannula amounts required during the surgery in half to reduce the number of the incision created on the patient's body, thereby reducing the surgery time, the hurt area and the damage to the joint tissue and lowering the probabilities of surgical complications and wound infection.

What is claimed is:

1. An arthroscopic cannula, comprising:
   a cannula body;
   a spacer disposed in the cannula body and extending axially along the cannula body to divide an internal space of the cannula body into a first chamber and a second chamber, wherein the spacer is configured to move perpendicularly to an axial direction of the cannula body to change cross-sectional areas of the first chamber and the second chamber; and
   a joint connecting with one end of the cannula body and having an interior intercommunicating with the first chamber and the second chamber.

2. The arthroscopic cannula as claimed in claim 1, wherein the spacer is in a form of a thin film, wherein each of two lateral edges of the spacer extends axially along the cannula body and connects with an inner surface of the cannula body, wherein the spacer has an end edge extending from one of the lateral edges to the other of the lateral edges, and wherein a length of the end edge is larger than an inner diameter of the cannula body.

3. The arthroscopic cannula as claimed in claim 2, wherein the two lateral edges of the spacer are diametrically opposite to each other in radial directions of the cannula body.

4. The arthroscopic cannula as claimed in claim 1, wherein the spacer is in a form of an elastic film, wherein each of two lateral edges of the spacer extends axially along the cannula body and connects with an inner surface of the cannula body.

5. The arthroscopic cannula as claimed in claim 4, wherein the two lateral edges of the spacer are diametrically opposite to each other in radial directions of the cannula body.

6. The arthroscopic cannula as claimed in claim 1, wherein the spacer is in a form of a flexible tube, wherein an outer circumferential length of the spacer is smaller than an inner circumferential length of the cannula body, and wherein an outer circumferential face of the spacer is partially connected to an inner surface of the cannula body.

* * * * *